US00PP18046P2

(12) United States Plant Patent
Koning

(10) Patent No.: US PP18,046 P2
(45) Date of Patent: Sep. 18, 2007

(54) LAVENDER PLANT NAMED 'TOSCANE'

(50) Latin Name: *Lavandula stoechas*
Varietal Denomination: Toscane

(75) Inventor: Lammert Koning, TJ Sappemeer (NL)

(73) Assignee: Koning Smit Holding N.V., Curacao (NL)

( * ) Notice: Subject to any disclaimer, the term of this patent is extended or adjusted under 35 U.S.C. 154(b) by 0 days.

(21) Appl. No.: 11/323,152

(22) Filed: Dec. 30, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

Upov CD–Rom Plant Variety Database 2006/04 for cultivar Toscane.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of Lavender plant named 'Toscane', characterized by its compact, upright, somewhat outwardly spreading and mounded plant habit; freely branching habit; dense and bushy plant form; early and freely flowering habit; large flowering period; and purple-colored flowers with light violet-colored terminal flower bracts.

2 Drawing Sheets

Botanical designation: *Lavandula stoechas.*
Cultivar denomination: 'Toscane'.

BACKGROUND OF THE INVENTION

The present Invention relates to a new and distinct cultivar of Lavender plant, botanically known as *Lavandula stoechas,* and hereinafter referred to by the name 'Toscane'.

The new Lavender is a product of a planned breeding program conducted by the Inventor in Sappemeer, The Netherlands. The objective of the breeding program was to create new Lavender cultivars that flowered early, attractive flowers and good garden performance.

The new Lavender originated from a cross-pollination made by the Inventor in May, 2000, of the *Lavandula stoechas* cultivar Fat Head, not patented, as the female, or seed, parent with a proprietary selection of *Lavandula stoechas* identified as NA-20, not patented, as the male, or pollen, parent. The new Lavender was discovered and selected by the Inventor as a single flowering plant within the progeny of the stated cross-pollination grown in a controlled environment in Sappemeer, The Netherlands.

Asexual reproduction of the new cultivar by terminal cuttings at Sappemeer, The Netherlands, since 2002, has shown that the unique features of this new Lavender are stable and reproduced true to type in successive generations.

SUMMARY OF THE INVENTION

Plants of the cultivar Toscane have not been observed under all possible environmental conditions. The phenotype may vary somewhat with variations in environment such as temperature and light intensity without, however, any variance in genotype.

The following traits have been repeatedly observed and are determined to be the unique characteristics of 'Toscane'.

These characteristics in combination distinguish 'Toscane' as a new and distinct cultivar:

1. Compact, upright, somewhat outwardly spreading and mounded plant habit.
2. Freely branching habit, dense and bushy plant form.
3. Early and freely flowering habit.
4. Long flowering period.
5. Purple-colored flowers with light violet-colored terminal flower bracts.

Plants of the new Lavender can be compared to plants of the female parent, the cultivar Fat Head. Plants of the new Lavender differ from plants of the cultivar Fat Head in the following characteristics:

1. Plants of the new Lavender flower about three weeks earlier than plants of the cultivar Fat Head.
2. Plants of the new Lavender are more freely flowering than plants of the cultivar Fat Head.
3. Plants of the new Lavender and the cultivar Fat Head differ in flower coloration.

Plants of the new Lavender can be compared to plants of the male parent selection. Plants of the new Lavender differ from plants of the male parent selection in the following characteristics:

1. Plants of the new Lavender and the male parent selection differ in foliage coloration.
2. Plants of the new Lavender and the male parent selection differ in flower coloration.

Plants of the new Lavender can be compared to plants of the Lavender cultivar Alexandra, not patented. In side-by-side comparisons conducted in Sappemeer, The Netherlands, plants of the new Lavender differed from plants of the cultivar Alexandra in the following characteristics:

1. Plants of the new Lavender were more compact and denser than plants of the cultivar Alexandra.

2. Plants of the new Lavender flowered earlier than plants of the cultivar Alexandra.
3. Plants of the new Lavender had more rounded inflorescences than plants of the cultivar Alexandra.

Plants of the new Lavender can also be compared to plants of the Lavender cultivar Anouk, disclosed in U.S. Plant patent application Ser. No. 11/113,371. In side-by-side comparisons conducted in Sappemeer, The Netherlands, plants of the new Lavender differed from plants of the cultivar Anouk in the following characteristics:

1. Plants of the new Lavender were more compact than and not as upright as plants of the cultivar Anouk.
2. Plants of the new Lavender flowered earlier than plants of the cultivar Anouk.
3. Plants of the new Lavender had more rounded inflorescences than plants of the cultivar Anouk.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Lavender.

The photograph on the first sheet comprises a side perspective view of a typical flowering plant of 'Toscane' grown in a container.

The photograph at the top of the second sheet comprises a close-up view of a typical inflorescence of 'Toscane'.

The photograph at the bottom of the second sheet is a close-up view of typical leaves of 'Toscane'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the winter and early spring in an outdoor nursery in Boskoop, The Netherlands for about 1.5 years in 12-cm containers. During the production of the plants, day temperatures ranged from 4° C. to 20° C. and night temperatures ranged from 0° C. to 14° C.

Botanical classification: *Lavandula stoechas* cultivar Toscane.

Parentage:

*Female, or seed, parent.*—*Lavandula stoechas* cultivar Fat Head, not patented.

*Male, or pollen, parent.*—Proprietary *Lavandula stoechas* selection identified as code number NA-20, not patented.

Propagation:

*Type cutting.*—Terminal cuttings.

*Time to initiate roots, summer and winter.*—About ten days at 18° C.

*Time to produce a rooted young plant, summer.*—About 60 days at 20° C.

*Time to produce a rooted young plant, winter.*—About 70 days at 20° C.

*Root description.*—Fine, fibrous.

*Rooting habit.*—Freely branching; dense.

Plant description:

*Form.*—Perennial. Compact, upright, somewhat outwardly spreading and mounded plant form. Freely branching habit, about 39 lateral branches; dense and bushy plant habit; moderately vigorous growth habit. Flowers in verticillasters on crowded spikes with showy terminal flower bracts.

*Plant height.*—About 29 cm.

*Plant width.*—About 30 cm.

*Lateral branch description.*—Length: About 11.7 cm. Diameter: About 2 mm. Internode length: About 8.5 mm. Strength: Strong. Aspect: Mostly upright to somewhat outwardly spreading. Texture: Densely tomentose. Color, immature: 138B. Color, mature: N199B.

*Foliage description.*—Arrangement: Opposite, simple; sessile. Length: About 3 cm. Width: About 4 mm. Shape: Linear. Apex: Acute. Base: Cuneate. Margin: Entire. Texture, upper and lower surfaces: Densely tomentose. Fragrance: Very aromatic, pungent. Venation pattern: Pinnate. Color: Developing foliage, upper surface: N138A. Developing foliage, lower surface: 138B. Fully expanded foliage, upper surface: 137A; venation, 138A. Fully expanded foliage, lower surface: Between 137A and N138B; venation, N138B.

Flower description:

*Flower arrangement and shape.*—Small single flowers in compact verticillasters on crowded spikes. Freely flowering, about 70 open flowers and flower buds per spike; flowers tubular with five lobes; inflorescences with showy terminal bracts.

*Natural flowering season.*—Long flowering period; continuous throughout the summer in The Netherlands.

*Flower longevity on the plant.*—Individual inflorescences last about ten days on the plant. Flowers not persistent.

*Fragrance.*—Spicy.

*Flower buds.*—Length: About 3 mm. Diameter: About 1.5 mm. Shape: Ovate. Color: 138C to 191B.

*Inflorescence size.*—Height: About 3.6 cm. Diameter, apex: About 1.3 cm. Diameter, base: About 2.5 cm.

*Flowers.*—Diameter: About 3.5 mm. Depth (height): About 9 mm.

*Petals.*—Arrangement: Five, fused into a tube. Length: About 8 mm. Width: About 1.5 mm. Shape: Roughly spatulate. Apex: Rounded. Margin: Entire. Texture, upper and lower surfaces: Smooth, glabrous. Color: When opening, upper and lower surfaces: Darker than 79A; towards the base, 85D. Fully opened, upper and lower surfaces: N186A; towards the base, 85D.

*Terminal flower bracts.*—Quantity/arrangement: About four at inflorescence apex. Length: About 1.8 cm. Width: About 7 mm. Shape: Obovate. Apex: Obtuse. Base: Cuneate. Margin: Entire; wavy. Texture, upper and lower surfaces: Smooth, glabrous. Color, upper and lower surfaces: 84A; midvein, 83C.

*Flower bracts.*—Arrangement: Each whorl of flowers subtended by a flower bract. Length: About 7 mm. Width: About 7 mm. Shape: Broadly rhomboidal. Apex: Broadly acute. Base: Cuneate. Margin: Entire. Texture, upper and lower surfaces: Densely tomentose. Color, upper and lower surfaces: 144C; venation, 141A.

*Calyx.*—Arrangement: Five sepals fused into a campanulate tube. Length: About 5 mm. Width: About 1.2 mm. Sepal shape: Linear. Sepal apex: Acute. Sepal margin: Entire. Sepal texture, upper and lower surfaces: Densely tomentose. Color, upper and lower surfaces: 138B; towards the base, 144C.

*Peduncles.*—Strength: Strong. Length: About 6.9 cm. Diameter: About 2 mm. Aspect: Mostly upright. Color: 138B.

*Reproductive organs.*—Stamens: Quantity per flower: Four. Filament length: About 0.5 mm. Anther shape: Reniform. Anther length: About 0.5 mm. Anther color: 17D. Pollen amount: Scarce. Pollen color: 17C. Pistils: Quantity per flower: One. Pistil length: About 4 mm. Stigma shape: Club-shaped. Stigma color: 79A to 79B. Style length: About 3.6 mm. Style color: Close to 155D. Ovary color: 145D.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from 0° C. to 40° C.

It is claimed:

1. A new and distinct cultivar of Lavender plant named 'Toscane', as illustrated and described.

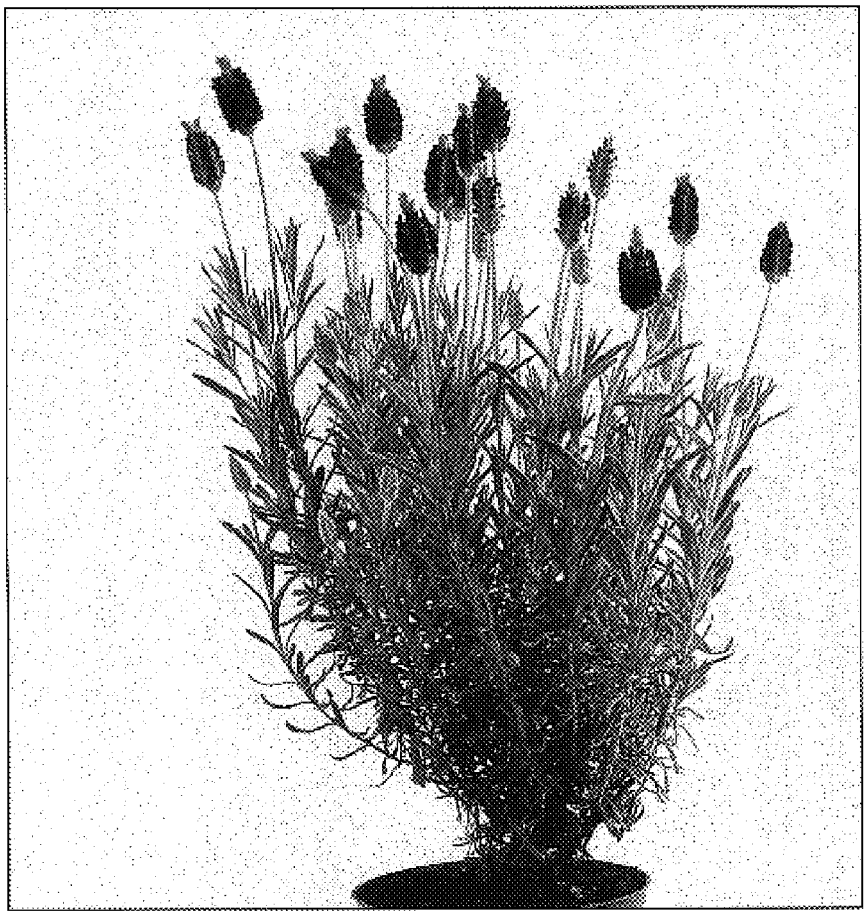

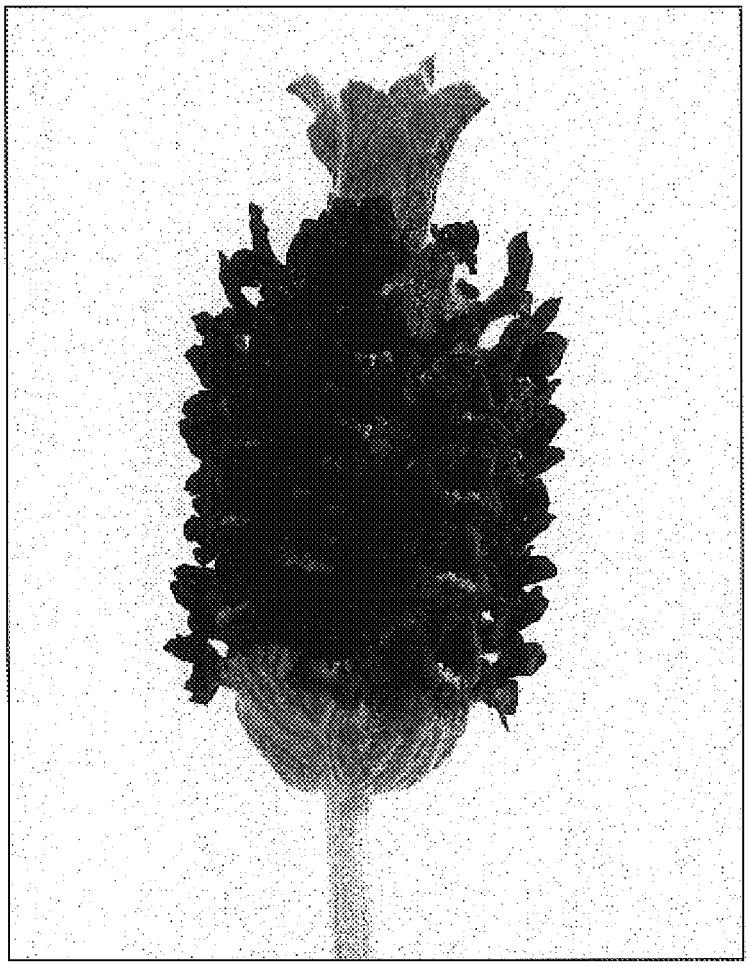
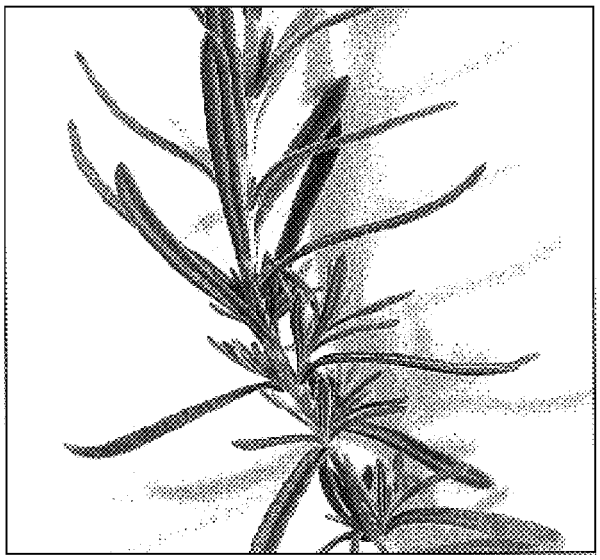

* * * * *